May 9, 1972 J. M. GARABEDIAN Plant Pat. 3,154
PLUM TREE
Filed April 15, 1970
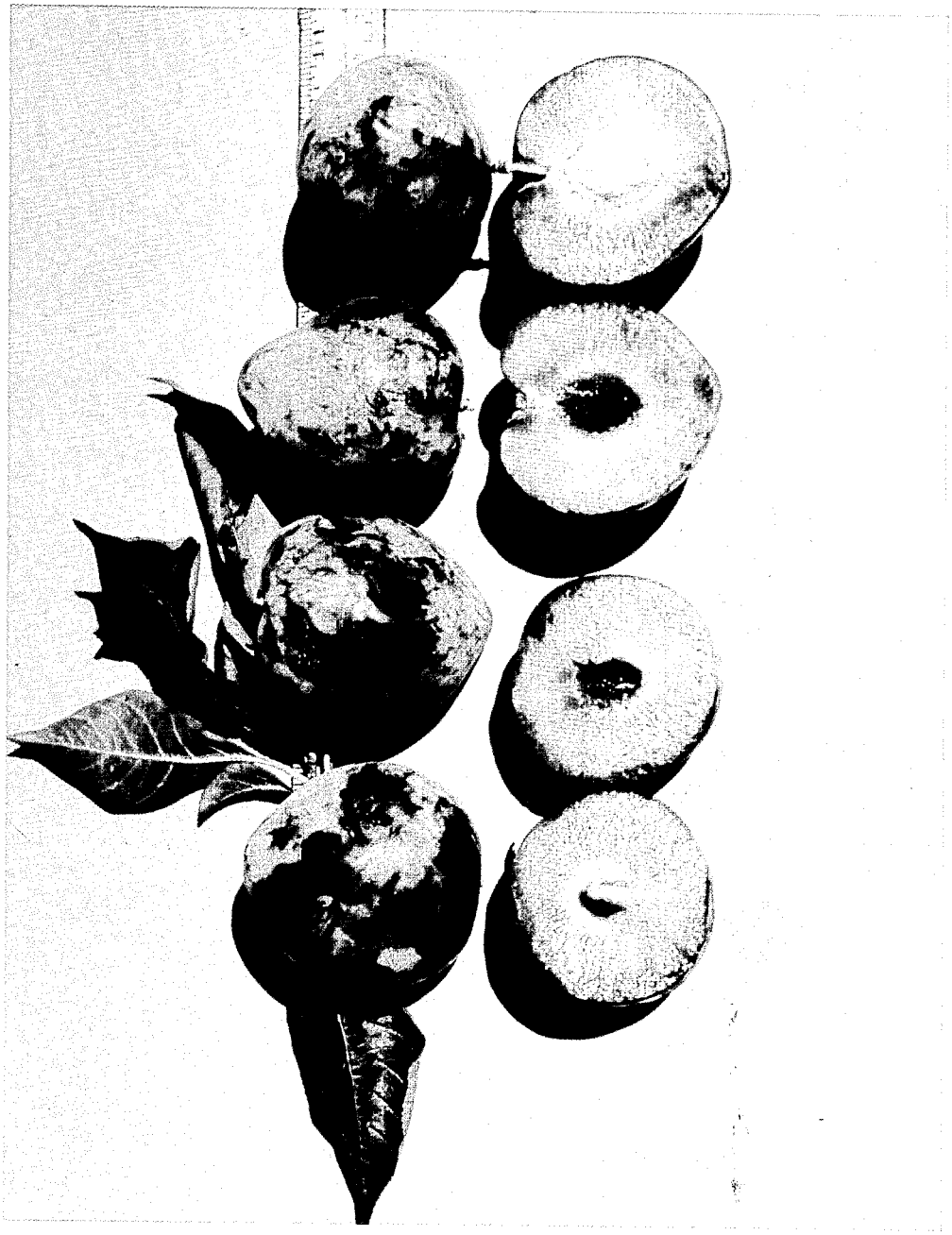
JOHN M. GARABEDIAN
INVENTOR
Huebner & Worrel
ATTORNEYS

United States Patent Office

Plant Pat. 3,154
Patented May 9, 1972

3,154
PLUM TREE

John M. Garabedian, 3158 Hamilton St., Fresno, Calif. 93712

Filed Apr. 15, 1970, Ser. No. 28,992
Int. Cl. A01h 5/03
U.S. Cl. Plt.—38 1 Claim The present invention relates to a plum tree and more particularly to a new and distinct variety thereof which is broadly characterized by its vigorous growth and regular bearing of unusually large plums having dark purple skin and brilliant red flesh.

The instant variety plum tree blooms about the same time as the Kelsey plum tree (unpatented) and its fruit ripens about the same time as the Kelsey which the instant variety most closely resembles. Its fruit distinguishes, however, from the Kelsey in being approximately fifty percent larger, having a dark purple skin which is nearly black when fully ripe more nearly resembling the skin of the fruit of the Queen Ann plum tree (unpatented), and a brilliant red flesh more similar to the flesh of the fruit of the Mariposa plum tree (Pat. No. 111). Furthermore, the skin of the fruit of the instant variety is substantially thicker and tougher than the skin of the fruit of the Kelsey affording greater resistance to bruising.

The new variety was developed by initially gathering seeds from a plurality of Kelsey plum trees, Queen Ann plum trees and Mariposa plum trees growing in a mixed orchard on my ranch on Church Avenue between Peach and Willow Avenues near Fresno, Calif. The Kelsey, Queen Ann and Mariposa trees were random pollinated by natural means. The seeds were planted in a hothouse without any effort to keep them segregated and produced a number of seedling plum trees. The seedlings were planted on my ranch in nursery rows in Janulary 1960 and fruited to a limited extent in 1962. That year the subject variety was selected for its exhibition of the above discussed distinctive and highly desirable characteristics. The selected seedling was asexually reproduced in 1962 by budding scions therefrom on seedlings of Mariposa plum tree rootstocks in an orchard at my above designated ranch. The budded trees fruited in July of 1966 and the fruit and tree characteristics resulting from such budding proved identical to those of the original seedling tree.

The accompanying drawing is a dye transfer color print of a photograph showing the leaves and several mature fruit of the subject variety with one of the fruit divided on its suture plane and another fruit divided in a plane right-angularly related to its suture plane to reveal flesh coloration and pit characteristics.

Referring more specifically to the pomological details of this new and distinct variety of plum tree, the following has been observed under the ecological conditions prevailing at my ranch near the city of Fresno, County of Fresno, and State of California. All major color plate identifications are by reference to the Maerz and Paul Dictionary of Color.

*Tree*

Size: Medium, vigorous, substantially upright but spreading and open with density determined by pruning methods; hardy, productive, and regular bearer.

Trunk: Medium to stocky, generally smooth with substantially vertical shallow striations in the bark.

Branches: Medium to slender, generally smooth; current season's dorsal growth being generally red while the ventral growth is generally green; year-old branches having striated greenish gray coloring over a dull green color. Lenticels—large size and numerous, large or more mature growth having a reddish color appearing mostly on the dorsal side of the branches with fewer and smaller lenticels appearing on the less mature branches.

Leaves:
- *Size.*—Medium to large.
- *Length.*—Average 5".
- *Width.*—Average 1⅞".
- *Shape.*—Oblanceolate, thick, glabrous, cuspidate at apex and pinnately veined.
- *Color.*—Dorsal surface, Yew green to Breuster green (24–L–10); ventral surface, Leek green (22–J–5).
- *Marginal form.*—Glandular, crenate.
- *Glands.*—Generally reniform with some globose, usually appearing in opposed pairs, large size, red color.
- *Petiole.*—Generally long, medium thick.
- *Stipules.*—Usually none.

Flower buds: Hardy. Size—generally small, plump, free with very light pubescence.

Flowers: Blooming period approximately the first week in March with full bloom occurring approximately at the end of the second week of March; relatively small; color of calyx cups—white; color of lobes—green; stamens averaging approximately 31 in number.

*Fruit*

Maturity when described, eating ripe, approximately July 28.

Size: Uniformly large, average axial diameter 2 3/16", average dimension transversely in suture plane 2⅜".

Form: Generally uniformly cordate in suture plane, generally symmetrical to oblique at the apex, and substantially globose in the plane right-angularly disposed from the suture plane.

Suture: Generally inconspicuous shallow line extending from the base and terminating at the apex.
- *Ventral surface.*—Slightly rounded.
- *Lips.*—Slightly unequal, not pronounced.
- *Cavity.*—Abrupt, deep, average depth 5/16", average breadth ⅝".
- *Base.*—Rounded to truncate.
- *Apex.*—Generally prolonged, pistil point apical.
- *Stem.*—Small to medium, average length ½", average diameter 5/32".

Skin: Thick, tough, bitter and tenacious to flesh.
- *Texture.*—Smooth with excellent resistance to shriveling.
- *Color.*—At basal and shoulders—Old Burgundy or (56–H–9) (56–E–7); at apex and cheeks—Flint (56–C–1), numerous small yellowish dots covered by bloom at basal end of cheek and shoulders; heavy bluish gray bloom—Denver Battleship gray (45–A–5).

Flesh:
- *Color.*—Clear brilliant red—Venetian Rose (5–L–1).
- *Surface of pit cavity.*—Dark red color—Indian red (7–L–6).
- *Juice.*—Moderate.
- *Texture.*—Firm, fine, crisp to meaty.
- *Fibers.*—Few, fine and tender.
- *Ripens.*—Generally even.
- *Flavor.*—Mild, vinuous.
- *Aroma.*—Very slight.
- *Eating quality.*—Very good.

Stone: Semi-free, adheres to flesh on ventral edges, relatively free on sides toward base. Retains short thread-like fibers along ridges of ventral side and retains short flesh tissue near ventral side.
- *Size.*—Generally large, average length 15/16", average width 11/16", average thickness ⅜".
- *Form.*—Elliptical.
- *Base.*—Usually straight.

*Hilum.*—Narrow, oval.
*Apex.*—Generally acute.
*Sides.*—Generally equal.
*Surface.*—Regularly furrowed near base and pitted above center.
*Ridges.*—Rounded toward apex.
*Pits.*—Relatively small, circular.
*Ventral edge.*—Thick with wing toward base.
*Dorsal edge.*—Narrow with shallow groove toward base.
*Color.*—Capucine Buff (9–E–5).
*Splitting tendency.*—None.
*Kernel.*—Wide at base with apex cuspidate; amygdalin moderate.

Use: Fresh market, dessert.
*Keeping quality.*—Good.
*Resistance to insects.*—Good.
*Resistance to disease.*—Good.
*Shipping quality.*—Good.

Although the new variety of plum tree possesses the described characteristics of the growing conditions in Fresno County, Calif. in the central portion of the San Joaquin Valley where the new variety was first observed, it is to be understood that variations of the usual magnitude in characteristics incident to environment and treatment are to be expected.

Having thus described and illustrated my new variety of plum tree, what is claimed as new and desired to be secured by Letters Patent is:

1. A new and distinct variety of plum tree substantially as illustrated and described which is characterized by its vigorous growth; and its regular and heavy bearing of unusually large plums which are approximately fifty percent larger than the plums from the Kelsey plum tree (unpatented), which it most nearly resembles, but from which it is distinguished in having a dark purple skin, more nearly resembling the skin of the fruit of the Queen Ann plum tree (unpatented), having a brilliant red flesh more similar to the flesh of the fruit of the Mariposa plum tree (Patent No. 111) and in its relataively thick, tough skin which has a greater resistance to shriveling and to bruising.

No references cited.

ROBERT E. BAGWILL, Primary Examiner

UNITED STATES PATENT OFFICE

CERTIFICATE OF CORRECTION

Patent No. Plant 3154 Dated May 9, 1972

Inventor(s) John M. Garabedian

It is certified that error appears in the above-identified patent and that said Letters Patent are hereby corrected as shown below:

Column 1, line 36, delete "Janulary" and substitute ---January---.

Column 2, line 19, between "period" and "approximately" insert ---beginning---.

Column 2, line 40, delete "5/6" " and substitute ---5/8"---.

Signed and Sealed this

Twenty-seventh Day of July 1976

[SEAL]

*Attest:*

RUTH C. MASON
*Attesting Officer*

C. MARSHALL DANN
*Commissioner of Patents and Trademarks*